United States Patent [19]

Simmons

[11] Plant 4,096

[45] Aug. 30, 1977

[54] APPLE TREE

[75] Inventor: Dan E. Simmons, Rogers, Ohio

[73] Assignee: Hilltop Orchards & Nurseries, Inc., Hartford, Mich.

[21] Appl. No.: 730,234

[22] Filed: Oct. 6, 1976

[51] Int. Cl.[2] ..... A01H 5/03

[52] U.S. Cl. ..... Plt./34

[58] Field of Search ..... Plt./34

*Primary Examiner*—Robert E. Bagwill

*Attorney, Agent, or Firm*—John R. Nesbitt

[57] ABSTRACT

This invention relates to a limb mutation of the Law strain of Red Rome apple, and differs therefrom by its dwarf habit and spurring.

1 Drawing Figure

This invention is a new and distinct cultivar of apple tree. It was discovered by applicant at his farm located in Section 33, Unity Township, Columbana County, Ohio, in March, 1973, as a limb mutation of the Law Strain of Red Rome. The new variety was asexually reproduced by Hilltop Nurseries and was given the experimental designation DS55. Reproduction was both by budding and grafting from the parent limb and these trees are growing at the Hilltop Nurseries farm at RFD #2, Hartford, Mich.

The new variety is a heavily spurred tree that is particularly characterized by the high percentage of shoot buds that form fruit spurs or short fruiting branches. The Law Strain of Red Rome does not exhibit these highly spurred characteristics. The new apple tree also exhibits dwarfing characteristics, consistently being as much as 20–25% smaller than said Law Strain of Red Rome variety. The internode spacing is, on the average, 5% less on the new variety compared with the Law Strain of Red Rome, and a much higher percentage of such nodes form a fruiting spur or branch.

The accompanying drawing (color photograph) shows, in

FIG. 1, a typical example of the fruit and foliage of DS55.

FIG. 2 shows two representative branches of DS55, particularly illustrating the close internode spacing.

A detailed description of the new variety is as follows:

TREE

Habit: Upright spreading, with strong spurring characteristics and strong dwarfing habit.

Bark: On fruiting wood, grayish-olive color, with very few slightly raised, but prominent lenticels. The bark is smooth, only slightly glossy to dull. Current season shoot growth is medium to slender and slightly zigzag. The shoot color is reddish-brown and very shiny with sparse lenticels that are slightly raised and moderately pubescent towards the tip.

LEAF

Color: Dark-green, healthy.

Shape: Somewhat ovate, upward folded, slightly wavy edges, leaf angle is very upright on new growth changing to more horizontal to inconsistent on fruiting wood and old growth.

Margin: Serrations are large, coarse and irregular and very pointed and sharp.

Aspect: Upper surface is a medium gloss moderate olive-green (Munsell chart-Hue of 5GY, value 3.5), lower surface lighter green and somewhat pubescent, with prominent raised veins and a midrib that is red to purplish-red — the red being most intense at the point of petiole attachment to the stem, the color intensity getting lighter and pinker as the midrib and veins move to the outer end and edges of the leaf.

Size: Current season growth, average 2 inches by 3½ inches and on fruiting spurs the average is 1½ inches by 3 inches.

Sepal: Very long and slender — ⅜ inch to ½ inch long on current season growth, and on older growth they average ¼ inch or less to nonexistent.

FLOWER

Buds: Bud scales are a distinctive purplish-red color and somewhat pubescent, the fruit bud is long, slender, cigar shaped, and hooked inward toward the shoot at the tip, which is not true of the Red Rome parent.

FRUIT

Typical Law Strain Red Rome fruit.

Flesh: Texture — medium grained, crisp.

Quality: Good, sub-acid, mild flavor.

Color: White with red spots at vascular bundles, and red epidermis adjacent skin.

Aroma: Faint, pleasant.

Maturity season: Same as Law Strain of Red Rome.

Keeping quality: Excellent both for storage and shipping, retaining quality for four to six months.

Use: This apple is good as a dessert apple and for commercial apple sauce.

I claim:

1. A new and distinct variety of apple trees substantially as described and illustrated in this application.

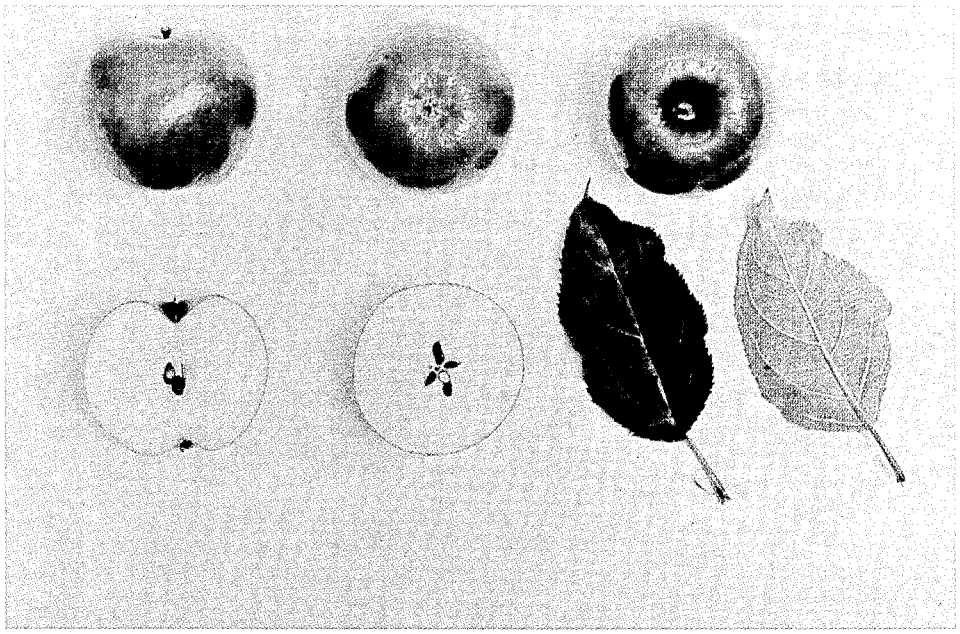
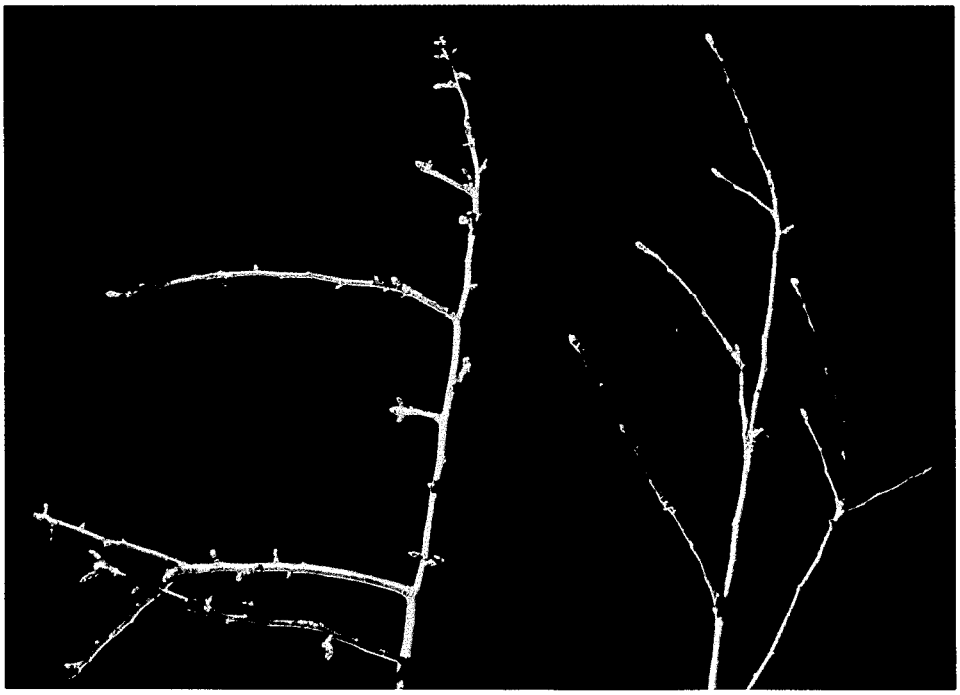

* * * * *